United States Patent
Caboche

(10) Patent No.: US 7,731,991 B2
(45) Date of Patent: Jun. 8, 2010

(54) NON-FOOD AND NON-PHARMACEUTICAL USE OF A SELECTED ANHYDROUS DEXTROSE COMPOSITION

(75) Inventor: Jean-Jacques Caboche, Drouvin le Marais (FR)

(73) Assignee: Roquette Freres, Lestrem (FR)

( * ) Notice: Subject to any disclaimer, the term of this patent is extended or adjusted under 35 U.S.C. 154(b) by 1258 days.

(21) Appl. No.: 11/260,268

(22) Filed: Oct. 28, 2005

(65) Prior Publication Data

US 2006/0110461 A1    May 25, 2006

(30) Foreign Application Priority Data

Oct. 29, 2004   (FR) .................................. 04 11603

(51) Int. Cl.
  *A61K 9/50*  (2006.01)
  *C08B 30/00*  (2006.01)
(52) U.S. Cl. .................... 424/499; 127/29; 424/489
(58) Field of Classification Search ............... None
  See application file for complete search history.

(56) References Cited

U.S. PATENT DOCUMENTS

| | | | |
|---|---|---|---|
| 4,059,460 A * | 11/1977 | Schollmeier et al. | 127/29 |
| 4,297,146 A | 10/1981 | Yoshinari et al. | |
| 4,931,101 A * | 6/1990 | Leleu | 127/60 |
| 5,076,853 A | 12/1991 | Leleu | |
| 6,083,535 A | 7/2000 | Chiba et al. | |
| 6,126,754 A | 10/2000 | Duflot | |
| 6,177,265 B1 | 1/2001 | Duflot | |
| 6,184,003 B1 | 2/2001 | Caboche | |
| 6,451,122 B1 * | 9/2002 | Moraly et al. | 127/30 |

2003/0092136 A1    5/2003 Delobeau

FOREIGN PATENT DOCUMENTS

| | | |
|---|---|---|
| DE | 2 144 406 | 3/1973 |
| EP | 0 202 999 A1 | 11/1986 |
| EP | 1 013 777 B1 | 6/2000 |
| EP | 1 041 161 A1 | 10/2000 |
| EP | 1 188 764 A1 | 3/2002 |
| FR | 2 266 458 | 10/1975 |
| FR | 2 366 361 | 4/1978 |
| FR | 2 446 068 | 8/1980 |
| FR | 2 762 616 | 10/1998 |
| FR | 2 791 700 | 10/2000 |
| FR | 2 791 701 | 10/2000 |
| FR | 2 791 703 | 10/2000 |
| FR | 2 830 021 | 3/2003 |
| GB | 2 189 676 A | 11/1978 |
| WO | WO 01/50853 A1 | 7/2001 |

OTHER PUBLICATIONS

S.K. Bhattacharjee—Evaluation of different types of sugar for improving postharvest life and quality of cut roses—Ann. agric. Res. 20(2): 159-165 (1999).

Umed Kumar Pun and Kazuo Ichimura—Role of Sugars in Senescence and Biosynthesis of Ethylene in Cut Flowers—JARQ 37(4), 219-224 (2003).

* cited by examiner

*Primary Examiner*—Traviss C McIntosh, III
(74) *Attorney, Agent, or Firm*—Young & Thompson

(57) ABSTRACT

The present invention relates to the non-food and non-pharmaceutical use of a powder anhydrous dextrose composition, characterized by the fact that the composition has:
  a) a particle size such that:
    at most 4% of its particles (expressed as a volume) have a size at most equal to 40 microns, and
    at most 8% of its particles (expressed as a volume) have a size at most equal to 100 microns,
  b) a hygroscopic index less than 1%, and
  c) an apparent density larger than 0.7 kg/l.

13 Claims, No Drawings

NON-FOOD AND NON-PHARMACEUTICAL USE OF A SELECTED ANHYDROUS DEXTROSE COMPOSITION

The present invention relates to the non-food and non-pharmaceutical use of an anhydrous dextrose composition, notably selected by its particle size and hygroscopicity characteristics.

An "anhydrous dextrose composition", refers to any solid composition of glucose which has, a) a water content at most equal to 1%, preferably at most equal to 0.9%, expressed relatively to the weight of said composition and b) a D-glucose content at least equal to 96%, preferably at least equal to 97%, expressed relatively to the dry weight of said composition.

This composition may have variable crystalline rates. Preferably, more than 90% by weight (dry weight/dry weight) of the glucose which it contains appear in an anhydrous crystalline form. Furthermore, this anhydrous form may be represented by very variable percentages of the alpha-anhydrous and beta-anhydrous forms, respectively. Preferably, the anhydrous alpha form accounts for more than 85% by weight (dry weight/dry weight) of anhydrous dextrose.

"Non-food and non-pharmaceutical use", refers to all uses in all fields of application, except the particular cases where the dextrose composition is intended to be directly ingested by humans or animals or intended to be directly injected to humans or animals.

This definition includes as non-limiting examples according to the invention, the uses of the dextrose composition for:
- synthesizing, via a chemical route, dextrose (or glucose) derivatives such as alkyl polyglucosides, alcenyl polyglucosides, mono- or di-acetone glucoses, coloring caramels, polyols, acids, vitamins, surfactants,
- synthesizing, via an enzymatic or microbiological route, the aforementioned derivatives and products,
- preparing fermentation, growth or isolation media for unicellular or pluricellular microorganisms (viruses, bacteria, yeasts, fungi, algae . . . ), cell or tissue culture media (cells/tissues of plant or animal origin),
- preparing compositions, in particular nutritive, dehydrating, conditioning, preservative and/or protective compositions, intended for treating plants or portions of plants (cut flowers, plants in earth or in pots, tobacco leaves . . . ),
- preparing coloring compositions, adjuvants for mineral binders (cements, grouts, concretes, plasters . . . ), additives or internal or external treatment compositions for plastic, metal, paper or textile materials; preparing agglomerates, either combustible or not, casting molds and cores, plaster boards, glues and adhesives, detergent compositions . . . .

The applicant company has noted that hitherto there was no dextrose composition on the market, even in relationship with the aforementioned fields of application, which simultaneously have the set of criteria hereafter:

1) a low hygroscopicity, not making indispensable a strict, and therefore costly check of the ambient humidity of the enclosures or packages in which said composition is to be contained, 2) particle size and flow characteristics adapted to standard transport, bagging, dosage, mixing, storing, cleaning, industrial and other methods and materials, not making indispensable the implementation of additional and/or costly means (a specific air feeding system, or hopper or silo with a specific internal coating), 3) a density also adapted to the aforementioned industrial operations and notably sufficiently high so as to limit i) the volume of the enclosures and of the packages in which said composition is to be contained, ii) the duration of the operations for loading/unloading said composition, and iii) industrial costs (reduction in transport costs, increase in production rates), 4) a low content of high fine particles or dust thereby limiting i) the risks of explosion or inhalation by the operators, ii) the problems of contamination by said particles of the surface of equipment, of packages, iii) the problems of electrostatic charges, 5) a sufficient purity so as to allow the user to attain his/her own industrial and commercial goals, notably in terms i) of purity of his/her own chemical or biological products obtained from dextrose, and ii) of yield from his/her own chemical or biological methods for treating or transforming dextrose, 6) a lowest possible ability to be untimely compressed in storage or transport enclosures, packages and this, before it being used in industry.

A selected dextrose composition has now been found capable of meeting the set of aforementioned criteria 1)-6) and consequently applicable in a multitude of uses such as those listed earlier.

Surprisingly and unexpectedly, the dextrose composition designed and developed by the applicant:
- not only avoids the industrial drawbacks either inherent to compositions based on atomized glucose syrups (limited D-glucose content, strong hygroscopicity, significant dust, poor flow, . . . ) or to dextrose monohydrate compositions (very high water content and relatively low density hence high transport and utilization costs . . . ),
- but also, because of its improved characteristics, most particularly in terms of particle size, reduced hygroscopicity and density, it may notably be used advantageously in industrial fields until then only reserved to dextrose monohydrate compositions, or technically inaccessible to all glucose solid compositions.

More specifically the present invention relates to the non-food and non-pharmaceutical use of a powder anhydrous dextrose composition characterized in that said composition has:

a) a particle size such that:
- at most 4% of its particles (expressed as a volume) have a size at most equal to 40 microns, and
- at most 8% of its particles (expressed as a volume) have a size at most equal to 100 microns, b) a hygroscopic index less than 1%, and c) an apparent density larger than 0.7 kg/l.

The particle size of the dextrose composition is conventionally measured by laser particle size analysis in a dry phase, for example on a particle size analyzer LASER LS 230 of the COULTER® brand fitted with a "dry powder" type dry phase module.

The hygroscopic index, expressed in %, corresponds to the difference in water content values of the dextrose composition, measured at equilibrium, on a same sample when the latter is placed at a temperature of 20° C. and at a relative humidity (RH) of 75% on the one hand and at 20° C. and at 50% RH on the other hand, it being understood that said sample is placed at 20° C., first at 50% RH, and then at 75% RH.

In the scope of the present application, the apparent density corresponds to the unpacked density of dextrose composition expressed in kg/l, and is measured with any standard method.

According to a first alternative, the dextrose composition which may be used according to the invention has a particle size such that at most 3%, preferably at most 2%, of its particles have a size at most equal to 40 microns. Advantageously, this value may be less than 1.5% and notably be between 0 and 1%.

According to another alternative, either combined or not with the previous one, said composition has a particle size such that at most 7%, preferably at most 6%, of its particles have a size at most equal to 100 microns. This value may be less than 5%, even being located between 0 and 3%.

According to a particular advantageous embodiment of the invention, said composition has a particle size such that:
 at most 1% of its particles have a size at most equal to 40 microns, and
 at most 2% of its particles have a size at most equal to 100 microns.

Moreover, the average diameter (in this case D (4,3)) of the constitutive particles of said dextrose composition may notably be larger than 250 microns, and less than 650 microns, in particular be between 280 and 540 microns. As an example, it may be located between 300 and 500 microns, notably between 350 and 500 microns.

According to other alternatives either combined or not with each other, or with the alternatives described earlier, said dextrose composition which may be used according to the invention, has:
 a hygroscopic index less than 0.5%, preferably less than 0.15%, and/or
 an apparent density larger than 0.75 kg/l, preferably between 0.78 and 0.95 kg/l.

Remarkably, the hygroscopic index may significantly be less than 0.15%, notably less than 0.1% and for example between 0.01 and 0.09%.

Independently, the applicant company has observed moreover that the anhydrous dextrose composition which may be used according to the invention, was able, at a very high RH, i.e., 85%, to contain less than 1% water, or even less than 0.5% water, at equilibrium.

The apparent density of said composition may advantageously be between 0.80 and 0.92 kg/l.

For certain uses, it is moreover desirable to make available to the user, an anhydrous dextrose composition as defined earlier, but having a D-glucose content even higher than 96 or 97%, and/or a water content even lower than 1 or 0.9%.

Following this, for the whole of the aforementioned alternatives, it may advantageously be provided that the dextrose composition has:
 a D-glucose content at least equal to 98%, preferably between 99 and 100% (dry weight/dry weight), and/or
 a water content less than 0.8%, preferably less than 0.5%, and even more preferentially between 0.01 and 0.45%.

As an example the D-glucose content may be between 99.5% and 100%. It may notably be larger than 99.7% (dry weight/dry weight). Glucose may in majority, or even quasi-exclusively, be present in a crystalline anhydrous form, whereby it itself may in majority or even quasi-exclusively, be an alpha anhydrous form.

The water content may, for example, be between 0.05 and 0.4%. It may notably be less than 0.2%.

Taking into account the characteristics of the anhydrous dextrose composition which may be used according to the invention, said composition generally appears as a powder which may be termed "free flowing powder".

Remarkably, according to a test which will be described elsewhere ("test T"), said composition may have improved flow characteristics as opposed to those of dextrose compositions generally put on the market, notably in the fields of application mentioned herein.

In particular, said composition may advantageously have, according to said T test, a flow index such as it will be defined elsewhere, less than 25 seconds, preferably between 8 and 24 seconds, and notably between 9 and 22 seconds. This index value may notably be between 10 and 18 seconds.

Further, in connection more particularly with the aforementioned criterion 6), the anhydrous dextrose composition which may be used according to the invention, has very low compressibility, or even a lack of compressibility.

In comparison with the EP 1 013 777 patent in the name of the applicant, said composition may notably have a compressibility, as determined according to the A test as described in paragraph 28, page 3, lines 30-35 of EP 1 013 777, of less than 80 Newtons, preferably less than 50 Newtons, and even more preferentially less than 30 Newtons.

This A test consists of measuring the force, expressed in Newton, which is representative of the compressibility of the investigated powder dextrose. Here this force expresses the crushing strength of a tablet which is cylindrical with convex faces (radius of curvature of 14 mm), of a diameter of 13 mm, of a thickness of 6 mm and of a weight of 0.764 g, i.e., and of an apparent density of 1.3 kg/l.

According to a particularly advantageous alternative, the anhydrous dextrose composition simultaneously has:
 a) a particle size such that:
  at most 4% of its particles (expressed as a volume) have a size at most equal to 40 microns, and
  at most 8% of its particles (expressed as a volume) have a size at most equal to 100 microns,
 b) a hygroscopic index less than 1%,
 c) an apparent density larger than 0.7 kg/l but also,
 d) a D-glucose content larger than 99.7% (dry weight/dry weight), and
 e) a water content less than 0.5%, preferably less than 0.2%.

To the applicant's knowledge, a dextrose composition characterized in this way is novel, independently of the applications (whether food, pharmaceutical applications) for which it may be intended.

Preferably, such a novel industrial product further has:
 an average diameter between 280 and 540 microns, and
 a compressibility, determined according to said A test, of less than 30 Newtons.

The anhydrous dextrose composition according to the invention or which may be used according to the invention, may be obtained by any means or any combination of means, capable of giving it the selected aforementioned characteristics a)-c) of particle size, hygroscopic index and apparent density, respectively, as well as possibly optional characteristics of D-glucose content, water content, average diameter and/or compressibility, also mentioned earlier.

It may notably be prepared from a very high glucose syrup (96% as expressed in dry weight/dry weight) as initially obtained according to general principles described in any of the patents FR 2 762 616, FR 2 791 700, FR 2 791 701, FR 2 791 703 or FR 2 830 021 in the name of the applicant, in particular from a syrup as initially obtained by applying membrane means, in particular nanofiltration membranes or chromatographic means.

Said syrup, whether obtained according to any of the aforementioned patents or not, may then advantageously be concentrated and crystallized by evaporation as described for example in the aforementioned FR 2 791 703 patent.

The resulting mass of crystals may for example then be dried on a rotary drum and/or a fluidized bed so that its water content is at most equal to 1%, for example of the order of 0.05 to 0.40%, notably in order to obtain a composition free or quasi-free of dextrose monohydrate and having a hygroscopic index as selected.

The thereby dried crystals may then undergo at least one physical separation step, for example at least one separation step on one or more industrial sieves, whereby the mesh size for each of them will be carefully selected so that a powder having not only the particle size but even the density characteristics according to the invention may be recovered.

Following this, a novel industrial means is now made available, capable of being advantageously used in the many aforementioned fields of application.

As an example, the selected anhydrous dextrose composition according to the invention finds an immediate industrial application in the preparation of compositions, notably nutritive, dehydrating, conditioning and preservative and/or protective compositions, intended for treating plants or portions of plants, for example cut flowers.

The use of glucose of dextrose is widely known in this field, as described for example in patents FR2 266 458, FR 2 446 068, GB 2,189,676, U.S. Pat. No. 6,083,535 or WO 01/50853.

In this kind of compositions, the glucose or dextrose is conventionally associated i.a. with at least one organic acid such as citric acid or succinic acid and with at least one biocidal agent.

Recent scientific studies have further investigated the role of sugars (possibly hydrogenated sugars) including glucose in various metabolic or physiological processes which may affect cut flowers (absorption of water, ethylene production, senescence . . . ). These notably are the following articles:

"Evaluation of Different Types of Sugars for Improving Postharvest Life and Quality of Cut Roses" of S. K. BHATTACHARJEE, Ann. Agric. Res. 20 (2): 159-165 (1999), and "Role of Sugars in Senescence and Biosynthesis of Ethylene in Cut Flowers" of U. K. PUN and K. ICHIMURA, JARQ 37(4), 219-224 (2003).

Among the aforementioned documents, only the article form S. K. BHATTACHARJEE especially contemplates the use of anhydrous dextrose, the other documents refer to glucose or dextrose very generally or mentioning by name dextrose monohydrate (FR 2 266 458).

Today, to the applicant's knowledge, only dextrose monohydrate is industrially and commercially used in this business sector.

In any case, none of these documents is concerned with developing a dextrose composition for cut flowers which would meet the whole of the aforementioned criteria 1)-6) (hygroscopicity, particle size/flow, density, fine particle content, purity, compressibility aspects).

And the applicant company has found that in this particular application as in other ones, notably those using dextrose monohydrate conventionally, with the anhydrous dextrose composition selected according to the invention, it will be possible not only to meet the aforementioned criteria 1)-6) but also to use it easily, as a mixture, with very diverse additives, even in the presence of water, and to provide formulated compositions themselves having desired or improved characteristics in terms of hygroscopicity, particle size, flow, density but also of compressibility, coloring and/or biological activity.

The invention will be able to be even better understood by the examples which follow and which are only given as purely illustrative examples.

EXAMPLE 1

An anhydrous dextrose composition according to the invention is prepared from a mass of dextrose crystals having a D-glucose content larger than 99.5% (dry weight/dry weight) and a water content of about 3%, said bulk of crystals having been obtained after conventional steps, conducted continuously, of crystallization by evaporation, water removal (separation of the crystals and of the mother liquors), washing of the crystals, than final water removal from the washed crystals.

These crystals are then dried on a rotary drum with hot air, so as to have a water content of less than 0.2%, and then cooled to room temperature on a fluidized bed.

They are then passed over a 1,000 μm sieve, the non-retained mass of crystals on said sieve being then sieved again but over 250 μm.

The anhydrous texture composition according to the invention represents the mass of dextrose crystals retained on this second sieve.

It appears as a free flowing white powder and having the characteristics hereafter, measured as described earlier:

D-glucose content ("D-GLU"): 100% volume of particles which have a size at most equal to 40 μm ("V 40μ"): 0% volume of particles which have a size at most equal to 100 μm ("V 100μ"): 0.2% average diameter ("D (4,3)"): 477 μm water content ("$H_2O$"): 0.15% water content, at equilibrium, at 20° C. and 50% RH ("EQU1"): 0.20% water content, at equilibrium, at 20° C. and 75% RH ("EQU2"): 0.23% hygroscopic index ("HYGRO")=EQ2−EQ1: 0.03%

APPARENT DENSITY ("DENSIT.")=0.87 kg/l.

The flow characteristics of said composition ("COMPOSITION A" hereafter) were investigated according to the T test described hereafter and based on the measurement of the time of flow of a determined amount of powder composition in a standardized funnel.

In a 2 litre plastic beaker, 1 kg of powder composition to be tested is weighed and slowly introduced into a standardized metal funnel, provided by CONTROLAB under reference "L 0060.1".

This funnel has a conical portion, the height of which is 240 mm and its internal diameter is 200 mm, said conical portion being extended by a rectilinear portion, the height of which is 100 mm and its internal diameter is 20 mm.

The end extremity of said rectilinear portion is fitted with a valve, in this case in the closed position, thereby obstructing this end extremity and thereby preventing flow of the powder.

After introducing COMPOSITION A into the thereby obstructed funnel in its end extremity, the system is left at rest for 5 minutes. Following this, the aforementioned valve is opened and a stopwatch is triggered simultaneously.

The stopwatch is stopped when the whole of the powder has finished flowing from the funnel. The time required for this flow is noted down. The flow index ("FLOW T") according to the T test which has just been described, expressed in seconds, corresponds to the average of 3 measured values for the same tested composition.

COMPOSITION A according to the invention thus has a FLOW T flow index of 14.32 seconds, it being specified moreover that said COMPOSITION A:

has a perfectly free flow, no assistance having been required for allowing or facilitating the flow of said COMPOSITION A, at any moment whatsoever of the T test, and does not generate any dust during the T test.

Moreover the applicant has evaluated the flow performances of the same COMPOSITION A but according to another test ("test T'"), similar to test T except that the 1 kg mass of COMPOSITION A introduced into the standardized funnel is replaced by the same mass of a formulated composition consisting of a powder mixture based on:

947.5 g of COMPOSITION A,
49.5 g of crystallized glucono-delta-lactone ("GDL") marketed by the applicant under the LYSACTONE® brand, and
1.5 g of powder sodium dichloroisocyanurate ("DCINa") dispersed beforehand in 1.5 g of water.

Such a mixture based on dextrose, an acidifying agent (GDL) and a biocidal agent (DCINa) may notably be used in the field of the compositions intended for treating plants or portions thereof, in particular cut flowers.

According to the T' test as described earlier, the powder mixture in vast majority based on COMPOSITION A, gave a flow index value ("FLOW T'") of 14.56 seconds (average of 3 values), i.e., equivalent to the FLOW T index value obtained for the single evaluated COMPOSITION according to test T (14.32 seconds).

And this occurs, like in the case of test T, without any flow assistance and without generating dust.

COMPOSITION A, with its physical characteristics may therefore advantageously be used for preparing formulated free flowing powder compositions.

Moreover, as noted by the applicant, it has very low compressibility (<30 Newtons according to the aforementioned test A) and may therefore, alone or within a powder mixture containing it, be stored, transported or conditioned without any significant risks of forming undesirable agglomerates.

EXAMPLE 2

Under the same conditions as those of example 1, the characteristics of:
two other anhydrous dextrose compositions according to the invention ("COMPOSITION B" and COMPOSITION C" hereafter),
a glucose composition not according to the invention, representative of an anhydrous dextrose of the market ("COMPOSITION T1"),
a glucose composition not according to the invention, representative of a dextrose monohydrate of the market ("COMPOSITION T2"), and
a glucose composition not according to the invention, representative of an atomized glucose syrup of the market ("COMPOSITION T3"),
were measured respectively.

The table below repeats the characteristics of each of the A, B, C compositions according to the invention and of the T1, T2 and T3 compositions outside the invention.

The above results show that the anhydrous dextrose compositions according to the invention such as compositions A, B and C, have remarkable characteristics in terms of particle size, hygroscopicity, density and flow, and may therefore be used advantageously, alone or as a mixture, as free flowing powders in as varied applications as those for synthesizing via a chemical or biotechnological route, substances, additives or active ingredients, for producing materials such as plaster boards, mineral binders or even for treating plants.

The invention claimed is:

1. A non-food and non-pharmaceutical product comprising a powder anhydrous dextrose composition, wherein said composition has:
    a) a particle size such that:
        at most 2% of its particles (expressed as a volume) have a size at most equal to 40 microns, and
        at most 7% of its particles (expressed as a volume) have a size at most equal to 100 microns,
    b) a hygroscopic index less than 1%,
    c) an apparent density larger than 0.7 kg/l,
    d) a D-glucose content of between 99 and 100%, expressed relatively to the dry weight of said composition, and
    e) a water content of between 0.01 and 0.4%, expressed relatively to the weight of said composition.

2. The product according to claim 1, wherein said dextrose composition has a particle size such that at most 6% of its particles have a size at most equal to 100 microns.

3. The product according to claim 1, wherein that said dextrose composition has a particle size such that:
    at most 1% of its particles have a size at most equal to 40 microns, and
    at most 2% of its particles have a size at most equal to 100 microns.

4. The product according to claim 1, wherein the average diameter of the particles of said dextrose composition is larger than 250 microns and less than 650 microns.

5. The product according to claim 4, wherein the average diameter of the particles is between 280 and 540 microns.

6. The product according to claim 1, wherein said dextrose composition has:
    a hygroscopic index less than 0.5%, and/or
    an apparent density larger than 0.75 kg/l.

|  | COMPOSITION | | | | | |
|---|---|---|---|---|---|---|
|  | A | B | C | T1 | T2 | T3 |
| D-GLU (%) | 100 | 99.9 | 100 | 99.5 | 99.0 | 94.7 |
| V 40μ (%) | 0 | 0 | 1.2 | 3.0 | 0.2 | 2 |
| V 100μ (%) | 0.2 | 0 | 6 | 16 | 1.2 | 4 |
| D (4, 3) (μm) | 477 | 375 | 409 | 270 | 250 | 550 |
| $H_2O$ (%) | 0.15 | 0.28 | 0.07 | 0.13 | 8.9 | 0.93 |
| EQU 1% | 0.20 | 0.28 | 0.10 | 0.18 | 9.60 | 0.93 |
| EQU 2% | 0.23 | 0.32 | 0.13 | 0.28 | 9.77 | 8.89 |
| HYGRO (%) | 0.03 | 0.04 | 0.03 | 0.10 | 0.17 | 7.96 |
| DENS. (kg/l) | 0.87 | 0.80 | 0.87 | 0.77 | 0.53 | 0.72 |
| FLOW T (s) | 14.32 | 15.68 | 20.51 | 20.02 | 27.36 | 19.03 |
| FLOW T' (s) | 14.56 | 17.08 | 13.50 | 20.45 (*) | 32.43 (**) | 18.50 (*) |

(*) lack of free flow - assisted flow
(**) production of dust

7. The product according to claim 6, wherein said dextrose composition has:

a hygroscopic index less than 0.15%, and/or an apparent density between 0.78 and 0.95 kg/l.

8. The product according to claim 1, wherein said dextrose composition has a flow index, measured according to a test T, of less than 25 seconds.

9. The product according to claim 8, wherein the flow index, is of between 8 and 24 seconds.

10. The product according to claim 9, wherein the flow index is of between 9 and 22 seconds.

11. The product according to claim 1, wherein said dextrose composition has a compressibility, measured according to a test A, of less than 80 Newtons.

12. The product according to claim 11, wherein the compressibility is less than 50 Newtons.

13. The product according to claim 12, wherein the compressibility is less than 30 Newtons.

* * * * *